United States Patent [19]
Shmulewitz

[11] Patent Number: 5,983,123
[45] Date of Patent: Nov. 9, 1999

[54] METHODS AND APPARATUS FOR PERFORMING ULTRASOUND AND ENHANCED X-RAY IMAGING

[75] Inventor: Ascher Shmulewitz, Mercer Island, Wash.

[73] Assignee: United States Surgical Corporation, Norwalk, Conn.

[21] Appl. No.: 09/099,165

[22] Filed: Jun. 18, 1998

Related U.S. Application Data

[63] Continuation-in-part of application No. 08/843,152, Apr. 11, 1997, which is a continuation of application No. 08/559,077, Nov. 16, 1995, Pat. No. 5,664,573, which is a continuation of application No. 08/277,894, Jul. 20, 1994, Pat. No. 5,479,927, which is a continuation-in-part of application No. 08/145,958, Oct. 29, 1993, Pat. No. 5,474,072.

[51] Int. Cl.[6] ................................. A61B 5/05; A61B 8/00
[52] U.S. Cl. ......................... 600/407; 600/437; 128/915
[58] Field of Search ........................... 600/407, 425–427, 600/437, 439, 443–445, 464; 128/915; 378/37, 11–14

[56] References Cited

U.S. PATENT DOCUMENTS

| Re. 30,397 | 9/1980 | King . |
|---|---|---|
| 2,707,662 | 5/1955 | Goldfield et al. . |
| 3,165,630 | 1/1965 | Bielat et al. . |
| 3,420,097 | 1/1969 | Battermann et al. . |
| 3,480,002 | 11/1969 | Flaherty et al. . |
| 3,556,081 | 1/1971 | Jones . |
| 3,589,361 | 6/1971 | Loper . |
| 3,609,355 | 9/1971 | Kwarzen . |
| 3,765,403 | 10/1973 | Brenden . |
| 3,921,442 | 11/1975 | Soloway . |

(List continued on next page.)

FOREIGN PATENT DOCUMENTS

| 105 812 | 4/1984 | European Pat. Off. . |
|---|---|---|
| 483 005 | 4/1992 | European Pat. Off. . |
| 581 704 | 2/1994 | European Pat. Off. . |
| 23 35 576 | 1/1975 | Germany . |
| 32 22 053 | 12/1983 | Germany . |
| 32 27 624 | 1/1984 | Germany . |
| 34 05 537 | 8/1985 | Germany . |
| 34 47 444 | 7/1986 | Germany . |
| 26 3228 | 12/1988 | Germany . |

(List continued on next page.)

OTHER PUBLICATIONS

Bruno D. Fornage, MD et al., Breast Masses: US–Guided Fine–Needle Aspiration Biopsy[1], Radiology, 162:409–414 (1987).

B.D. Fornage, MD et al., "Ultrasound–Guided Needle Biopsy of the Breast and Other Interventional Procedures", vol. 30, No. 1, pp. 167–185 (Jan. 1992).

Darla Haight et al., "Radiologists Spread Their Wings: A Look at the Possibilities in STereotactic Breast Biopsy", Admin. Rad. J., pp. 87–89 (Nov. 1987).

E. Azavedo et al., "Stereotactic Fine–Needle Biopsy in 2594 Mammographically Detected Non–Palable Lesions", The Lancet, p. 1033–1036 (May 1989).

Eva Rubin, MD, "Breast Cancer in the 90's", Applied Radiology, pp. 23–26 (Mar. 1993).

(List continued on next page.)

*Primary Examiner*—Franics J. Jaworski

[57] ABSTRACT

Apparatus is provided that combines radiography equipment with an ultrasonic transducer to generate ultrasonic images of the internal structure of biological tissue that are in registration with an X-ray image. The apparatus includes an examination table having a radiolucent and sonolucent window for imaging the biological tissue with an ultrasound and X-ray subsystems without moving the patient. In alternative embodiments, the ultrasound transducer may be an annular array transducer mounted on a moveable or a linear array of ultrasonic transducing elements. The X-ray images are preferably generated digitally using a line X-ray source and detector.

21 Claims, 3 Drawing Sheets

U.S. PATENT DOCUMENTS

| | | |
|---|---|---|
| 3,939,696 | 2/1976 | Kossoff . |
| 3,963,933 | 6/1976 | Henkes, Jr. . |
| 3,971,950 | 7/1976 | Evans et al. . |
| 3,973,126 | 8/1976 | Redington et al. . |
| 3,990,300 | 11/1976 | Kossoff . |
| 3,991,316 | 11/1976 | Schmidt et al. . |
| 4,021,771 | 5/1977 | Collins et al. . |
| 4,051,380 | 9/1977 | Lasky . |
| 4,058,114 | 11/1977 | Soldner . |
| 4,094,306 | 6/1978 | Kossoff . |
| 4,099,880 | 7/1978 | Kano . |
| 4,167,180 | 9/1979 | Kossoff . |
| 4,206,763 | 6/1980 | Pederson . |
| 4,249,541 | 2/1981 | Pratt . |
| 4,285,010 | 8/1981 | Wilcox . |
| 4,343,799 | 8/1982 | Heckler . |
| 4,347,850 | 9/1982 | Kelly-Fry et al. . |
| 4,363,326 | 12/1982 | Kopel . |
| 4,369,284 | 1/1983 | Chen . |
| 4,402,324 | 9/1983 | Lindgren et al. . |
| 4,433,690 | 2/1984 | Green et al. . |
| 4,434,799 | 3/1984 | Taenzer . |
| 4,455,872 | 6/1984 | Kossoff et al. . |
| 4,465,069 | 8/1984 | Barbier et al. . |
| 4,469,106 | 9/1984 | Harui . |
| 4,485,819 | 12/1984 | Igl . |
| 4,497,325 | 2/1985 | Wedel . |
| 4,501,278 | 2/1985 | Yamaguchi et al. . |
| 4,527,569 | 7/1985 | Kolb . |
| 4,541,436 | 9/1985 | Hassler et al. . |
| 4,545,385 | 10/1985 | Pirschel . |
| 4,573,180 | 2/1986 | Summ . |
| 4,579,123 | 4/1986 | Chen et al. . |
| 4,583,538 | 4/1986 | Onik et al. . |
| 4,592,352 | 6/1986 | Patil . |
| 4,599,738 | 7/1986 | Panetta et al. . |
| 4,608,989 | 9/1986 | Drue . |
| 4,613,122 | 9/1986 | Manabe . |
| 4,613,982 | 9/1986 | Dornheim et al. . |
| 4,618,213 | 10/1986 | Chen . |
| 4,618,973 | 10/1986 | Lasky . |
| 4,625,555 | 12/1986 | Fujii . |
| 4,671,292 | 6/1987 | Matzuk . |
| 4,681,103 | 7/1987 | Boner et al. . |
| 4,686,997 | 8/1987 | Oloff et al. . |
| 4,722,346 | 2/1988 | Chen . |
| 4,727,565 | 2/1988 | Ericson . |
| 4,733,661 | 3/1988 | Palestrant . |
| 4,735,215 | 4/1988 | Goto et al. . |
| 4,750,487 | 6/1988 | Zanetti . |
| 4,774,961 | 10/1988 | Carr . |
| 4,784,134 | 11/1988 | Arana . |
| 4,791,934 | 12/1988 | Brunnett . |
| 4,821,727 | 4/1989 | Levene et al. . |
| 4,844,080 | 7/1989 | Frass et al. . |
| 4,862,893 | 9/1989 | Martinelli . |
| 4,869,247 | 9/1989 | Howard, III et al. . |
| 4,875,478 | 10/1989 | Chen . |
| 4,890,311 | 12/1989 | Saffer . |
| 4,898,178 | 2/1990 | Wedel . |
| 4,899,756 | 2/1990 | Sonek . |
| 4,911,173 | 3/1990 | Terwilliger . |
| 4,930,143 | 5/1990 | Lundgren et al. . |
| 4,940,061 | 7/1990 | Terwilliger et al. . |
| 4,944,308 | 7/1990 | Akerfeldt . |
| 4,953,558 | 9/1990 | Akerfeldt . |
| 4,962,515 | 10/1990 | Kopans . |
| 4,962,752 | 10/1990 | Reichenberger et al. . |
| 4,966,152 | 10/1990 | Gäet al. . |
| 4,981,142 | 1/1991 | Dachman . |
| 5,003,979 | 4/1991 | Merickel et al. . |
| 5,007,428 | 4/1991 | Watmough . |
| 5,029,193 | 7/1991 | Saffer . |
| 5,056,523 | 10/1991 | Hotchkiss, Jr. et al. . |
| 5,072,721 | 12/1991 | Weiler et al. ............................ 378/209 |
| 5,078,142 | 1/1992 | Siczek et al. . |
| 5,078,149 | 1/1992 | Katsumata et al. . |
| 5,083,305 | 1/1992 | Tirelli et al. . |
| 5,095,910 | 3/1992 | Powers . |
| 5,099,503 | 3/1992 | Strömmer . |
| 5,107,843 | 4/1992 | Aarnio et al. . |
| 5,113,420 | 5/1992 | Davis, Jr. et al. . |
| 5,158,088 | 10/1992 | Nelson et al. . |
| 5,199,056 | 3/1993 | Darrah . |
| 5,205,297 | 4/1993 | Montecalvo et al. . |
| 5,219,351 | 6/1993 | Teubner et al. . |
| 5,260,871 | 11/1993 | Goldberg . |
| 5,262,468 | 11/1993 | Chen . |
| 5,273,435 | 12/1993 | Jacobson . |
| 5,280,427 | 1/1994 | Magnusson et al. . |
| 5,305,365 | 4/1994 | Coe . |
| 5,318,028 | 6/1994 | Mitchell et al. . |
| 5,361,768 | 11/1994 | Webler et al. . |
| 5,379,769 | 1/1995 | Ito et al. . |
| 5,386,447 | 1/1995 | Siczek . |
| 5,396,897 | 3/1995 | Jain et al. . |
| 5,411,026 | 5/1995 | Carol . |
| 5,415,169 | 5/1995 | Siczek et al. . |
| 5,426,685 | 6/1995 | Pellegrino et al. . |
| 5,433,202 | 7/1995 | Mitchell et al. . |
| 5,447,154 | 9/1995 | Cinquin et al. . |
| 5,450,851 | 9/1995 | Hancock . |
| 5,474,072 | 12/1995 | Shmulewitz . |
| 5,479,927 | 1/1996 | Shmulewitz . |
| 5,487,387 | 1/1996 | Trahey et al. . |
| 5,488,952 | 2/1996 | Schoolman . |
| 5,499,989 | 3/1996 | LaBash . |
| 5,506,877 | 4/1996 | Niklason et al. . |
| 5,522,787 | 6/1996 | Evans . |
| 5,524,636 | 6/1996 | Sarvazyan et al. . |
| 5,594,769 | 1/1997 | Rellegrino et al. . |
| 5,595,177 | 1/1997 | Mena et al. . |
| 5,603,326 | 2/1997 | Richter ................................... 600/443 |
| 5,609,152 | 3/1997 | Pellegrino et al. . |
| 5,640,956 | 6/1997 | Getzinger et al. . |
| 5,660,185 | 8/1997 | Shmulewitz et al. . |
| 5,664,573 | 9/1997 | Shmuulewitz et al. . |
| 5,776,062 | 7/1998 | Nields ..................................... 600/407 |
| 5,840,022 | 11/1998 | Richtes ................................... 600/407 |

FOREIGN PATENT DOCUMENTS

| | | |
|---|---|---|
| 38 29 259 | 3/1989 | Germany . |
| 40 37 387 | 5/1992 | Germany . |
| 70 23 909 | 3/1993 | Germany . |
| 896 539 | 4/1980 | U.S.S.R. . |
| 2 094 590 | 9/1982 | United Kingdom . |
| 83/02053 | 6/1983 | WIPO . |
| 88/08272 | 11/1988 | WIPO . |
| 89/11248 | 11/1989 | WIPO . |
| 94/21189 | 9/1994 | WIPO . |
| 95/11627 | 5/1995 | WIPO . |

OTHER PUBLICATIONS

Ellen B. Mendelson, MD, "Ultrasound Secures Place in Breast Ca Management", Diagnostic Imaging, pp. 120–129 (Apr. 1991).

Ferris H. Hall, MD, "Mammographic Second Opinions Prior to Biopsy of Nonpalpable Beast Lesions", Arch Surg, vol. 125, pp. 298–299 (Mar. 1990).

Gunilla Svane, MD., "Stereotactic Needle Biopsy", Dept. of Dianostic Radioloyg at the Karolinska Hospital, Stockholm, Sweden (1987).

Gillian Newstead, MD., "When and When Not to Biopsy the Breast", Diagnostic Imaging, pp. 111–116, (Mar. 1993).

Ingvar Andersson, MD, "Medical Radiography and Photography", vol. 62, No. 2, pp. 2–41 (1986).

Jan Bolmgren, et al., "Stereotaxic Instrument for Needle Biopsy of the Mamma", (Sweden) J. Radiology, 129:121–125 (Jul. 1977).

Kumbiz Dowlatshahi, MD, Breast Care: "The Needle Replaces The Knife" (Exploring Sterotactic Guided Needle Biopsy), Admin. Radiology, pp. 28–31 (Jun. 1989).

K. Dowlatshahi, MD, "Palpable Breast Tumors: Dianosis with Stereotaxic Localization and Fine–Needle Aspiration[1]", Radiology 170, No. 2, pp. 427–433 (Feb. 1989).

Ralph Mösges et al., "Multimodal Information for Computer–Integrated Surgery", Mösges & Lavallëe: Multimodal Information for CIS/Data Acquistion & Segmentation, pp. 5–19.

Rachel F. Brem, MD et al., "Template Breast US[1]", Radiology 184:872–874 (Sept. 1992).

Steve H. Parker, MD et al., "Percutaneous Large–Core Breast Biopsy: A Multi–institutional Study[1]", Radiology vol. 193, No. 2, pp. 359–364 (Nov. 1994).

S.H. Parker, MD et al., "Large–Core Breast Biopsy Offers Reliable Diagnosis", Diagnostic Imaging, 8 pages (Oct. 1990).

S.H. Parker, MD et al., "US–guided Automated Large–Core Breast Biospy[1]", Radiology, 187:507–511 (May 1993).

P.N.T. Wells et al., "Tumor detection by ultrasonic Doppler blood–flow signals", Ultrasonics, pp. 231–232 (Sep. 1977).

Valerie P. Jackson, MD, "The Role of US in Breast Imaging[1]", Radiology 177:305–311 RSNA (Nov. 1990).

W. Phil Evans, MD et al., "Needle Localization and Fine–Needle Aspiration Biopsy of Nonpalpable Breast Lesions with use of Standard and Stereotactic Equipment", Radiology, 173:53–56 (1989).

William F. Conway, MD et al., "Occult Breast Masses: Use of a Mammographic Localizing Grid for US Evaluation[1]", Radiology, 181: 143–146 (1991).

METHODS AND APPARATUS FOR PERFORMING ULTRASOUND AND ENHANCED X-RAY IMAGING

CROSS-REFERENCE TO RELATED APPLICATIONS

This application is a continuation-in-part of U.S. patent application Ser. No. 08/843,152 filed Apr. 11, 1997 which is a continuation of U.S. patent application Ser. No. 08/559,077, filed Nov. 16, 1995, now U.S. Pat. No. 5,664,573, which is a continuation of U.S. patent application Ser. No. 08/277,894, filed Jul. 20, 1994, now U.S. Pat. No. 5,479,927, which is a continuation-in-part of U.S. patent application Ser. No. 08/145,958, filed Oct. 29, 1993, now U.S. Pat. No. 5,474,072.

BACKGROUND

1. Technical Field

The present disclosure relates to methods and apparatus for imaging biological tissue employing both X-ray and ultrasound technology to provide enhanced diagnostic capability. In particular, the present disclosure provides a combined ultrasonic and an X-ray imaging system that provides registered X-ray and ultrasound images.

2. Background of Related Art

The use of X-ray technology for providing two-dimensional images of biological tissue for diagnosis of carcinoma or other tissue abnormalities is well known. However, X-ray imaging has a number of limitations which are universally recognized by radiologists, such as, for example, that X-ray images provide only a two-dimensional image of a three-dimensional object. Thus, although a potential area of concern may be indicated, the precise location of the subject area within the tissue may be uncertain.

In addition to conventional radiography machines, an apparatus has been developed that employs ultrasound technology for imaging biological tissue. Ultrasound imaging devices display echoes received from a transducer as brightness levels proportional to the energy reflected by the tissue components. These brightness levels are displayed at the appropriate echo range and transducer position or orientation, resulting in a cross-sectional image of the object in a plane perpendicular to the transducer emitting face.

Heretofore, the advantages offered by ultrasound technology have long been recognized by the medical community, construction of previously known radiography and sonography equipment has prevented combination of these two technologies.

Specifically, polycarbonates such as Lexan®, are typically used in radiography machines because of their tensile strength and transparency to X-ray radiation. These materials are substantially acoustically opaque, however, and tend to distort most ultrasonic signals traversing these materials, as described in U.S. Pat. No. 5,479,927 which is herein incorporated by reference. On the other hand, the compression plates used in previously known ultrasound devices, for example, as described in U.S. Pat. No. 3,765,403, are composed of materials such as polystyrene or polyurethane, which have insufficient tensile strength for use in radiography equipment.

Several previously known devices, such as described, for example, in WO Publication No. 83/02053, have sought to achieve spatial registration between X-ray and ultrasound images. Such devices, however, have required movement of the tissue between the X-ray and ultrasound imaging steps, thereby preventing accurate correlation of the two images.

In view of the foregoing drawbacks of previously known imaging apparatus and methods, it would be desirable to provide an apparatus and methods for providing registered X-ray and ultrasound images of biological tissue.

SUMMARY

In view of the foregoing, it is an object of the present disclosure to provide apparatus and methods for providing registered X-ray and ultrasound images of biological tissue.

It is another object of the present disclosure to provide apparatus for performing combined radiography and ultrasound imaging (hereinafter "sonoradiography") apparatus that contains a window that is both radiolucent and sonolucent, so that both X-ray and ultrasound images of biological tissue may be obtained without intervening movement of the biological tissue.

It is a further object of the present disclosure to provide apparatus for moving an ultrasound transducer across a window to provide ultrasound images of biological tissue at preselected intervals.

It is a further object of the disclosure to provide an ultrasound transducer and X-ray imaging apparatus for use in sonoradiography apparatus, that provides a plurality of ultrasound images of the biological tissue that are in registration with the X-ray images.

These and other objects of the disclosure are accomplished by providing a combined X-ray and ultrasound imaging system including an examination table having a sonolucent and radiolucent window. In a preferred embodiment, images are obtained using a digital scanning X-ray detector and ultrasound transducer located in parallel on a moveable gantry positioned beneath the window.

Either before or after the X-ray exposure of tissue positioned on the window, an ultrasound transducer is translated by the gantry to generate a plurality of sectional views of the biological tissue. An X-ray image is then generated by moving the gantry (and the X-ray tube) in a continuous scan over the patient to digitally generate an X-ray image. The X-ray and ultrasound images are then processed by a microprocessor-based workstation to provide registered two-dimensional views, or holographic views, of the internal features of the tissue.

BRIEF DESCRIPTION OF THE DRAWINGS

Further features of the disclosure, its nature and various advantages will be more apparent from the accompanying drawings and the following detailed description of the preferred embodiments, in which.

DETAILED DESCRIPTION OF THE PREFERRED EMBODIMENTS

In the illustrative preferred embodiment described hereinbelow, the X-ray imaging subsystem is a scanningtype system, in which a linear X-ray source is moved in synchrony with a linear X-ray detector to generate a two-dimensional X-ray image. As will be apparent to one of skill in the art of radiography, other X-ray imaging apparatus also may be advantageously employed in practicing the present disclosure.

Figure 1:
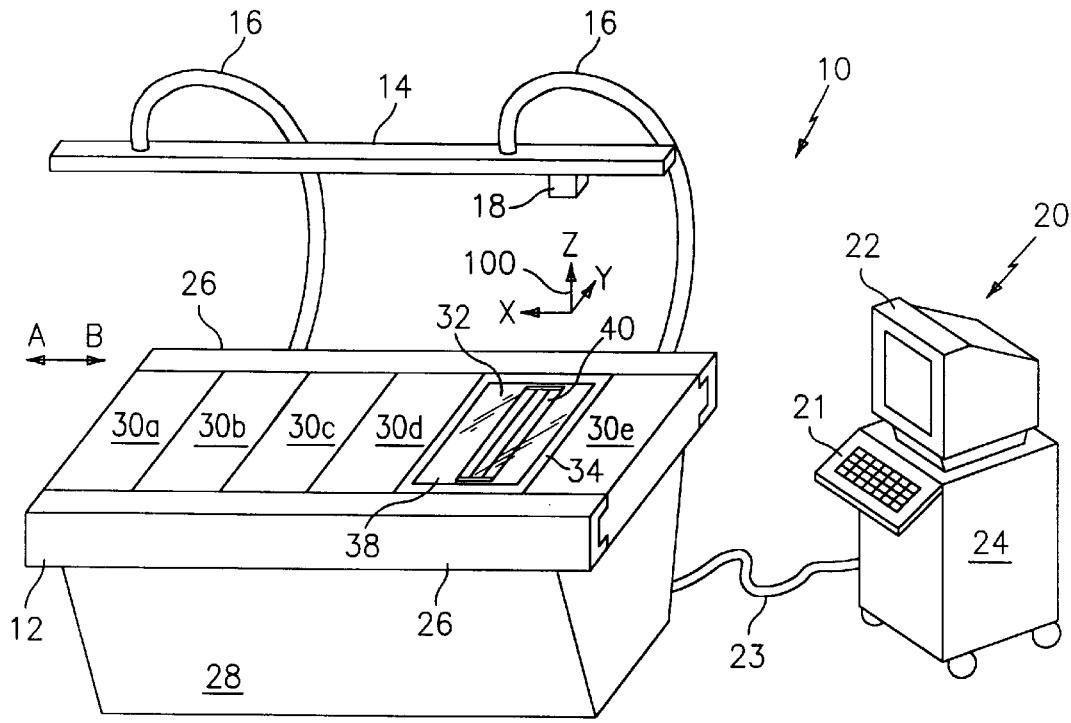
FIG. 1 is a perspective view of apparatus constructed in accordance with the principles of the present disclosure.

Referring to FIGS. 1 and 2, apparatus 10 is constructed in accordance with the principles of the present disclosure. Apparatus 10 includes examination table 12, horizontal rail 14 coupled to vertical support columns 16 and X-ray tube 18 movably suspended from horizontal rail 14. Control station 20 includes keyboard 21, monitor 22 and a microprocessor and related electronics housed in cart 24 that are electrically coupled to examination table 12 via cable 23. Control station 20 controls operation of the X-ray and ultrasound imaging systems of apparatus 10 and acquires, stores and processes data output by those subsystems.

Examination table 12 includes side rails 26 supported by base 28. Removable table sections 30a–30e and scanning section 32 are disposed in side rails 26 for sliding movement in directions A and B. Scanning section 32 includes frame 34 that slides in side rails 26, and which includes gantry 40 disposed beneath window 38. In accordance with the present disclosure, gantry 40 houses X-ray detector 42 and ultrasound transducer array 44. As described hereinbelow, gantry 40 is arranged to move from one end of scanning section 32 to the other end of the scanning section.

In a preferred embodiment, examination table 12 is configured so that scanning section 32 may be readily moved to a selected position on the table, for example, to permit imaging of a desired portion of a patient's body. To accomplish this, the clinician removes a suitable number of table sections 30a–e from between side rails 26, and then slides frame 34 of scanning section 32 to the desired position. The clinician then inserts the removed table sections back into the side rails (from the opposite end of the table), to provide a support surface for the patient. Thus, for example, if in FIG. 1 it is desired to image a patient's lower extremity, table sections 30e may be removed in direction B, scanning section 32 may be moved flush to the end of the table in direction B, and then table section 30e may be inserted back into side rails 26 adjacent table section 30a. Accordingly, scanning section 32 may be moved to any position desired on examination table 12.

The radiography components of apparatus 10, i.e., X-ray tube 18 and digital X-ray detector 42 may include the features described hereinafter, but otherwise are constructed as in previously known devices. As in previously known radiography equipment, the location of horizontal and vertical supports 14 and 16, and X-ray tube 18 may be selectively and movably determined, either manually or using a motorized arrangement which is per se known.

While the illustrative embodiments provided herein refer to digital (film-less) X-ray systems, it will of course be understood by one familiar with radiology that convention film X-ray detectors could be employed. It is sufficient for purposes of practicing the present disclosure that X-ray radiation emitted from an X-ray source pass through biological tissue positioned on window 38 to form an image on X-ray detector 42, whether an X-ray film or a digital X-ray detector. The X-ray source can be either a two dimensional X-ray tube, a line source or a point source.

In a preferred embodiment, X-ray tube 18 is a line source, generated, for example, using a previously known X-ray tube and a slit, as described in Fraser et al., "Digital Imaging of the Chest", *Radiology*, May 1989, pp. 297–307, or by other previously known methods, such as described in U.S. Pat. Nos. 4,692,937 and 4,696,022, which are incorporated herein by reference. Digital X-ray detector 42 is also preferably a line detector having, e.g., CCD detector elements, such as the detectors described in the above-incorporated references, or in U.S. Pat. Nos. 4,905,265, 5,043,582 and 5,220,170, which are also incorporated herein by reference. Where X-ray tube 18 provides a line source of X-rays which are received by X-ray detector 42, X-ray tube 18 may be mounted for travel along horizonal support rail 14 in synchronization with gantry 40.

Figure 2A:
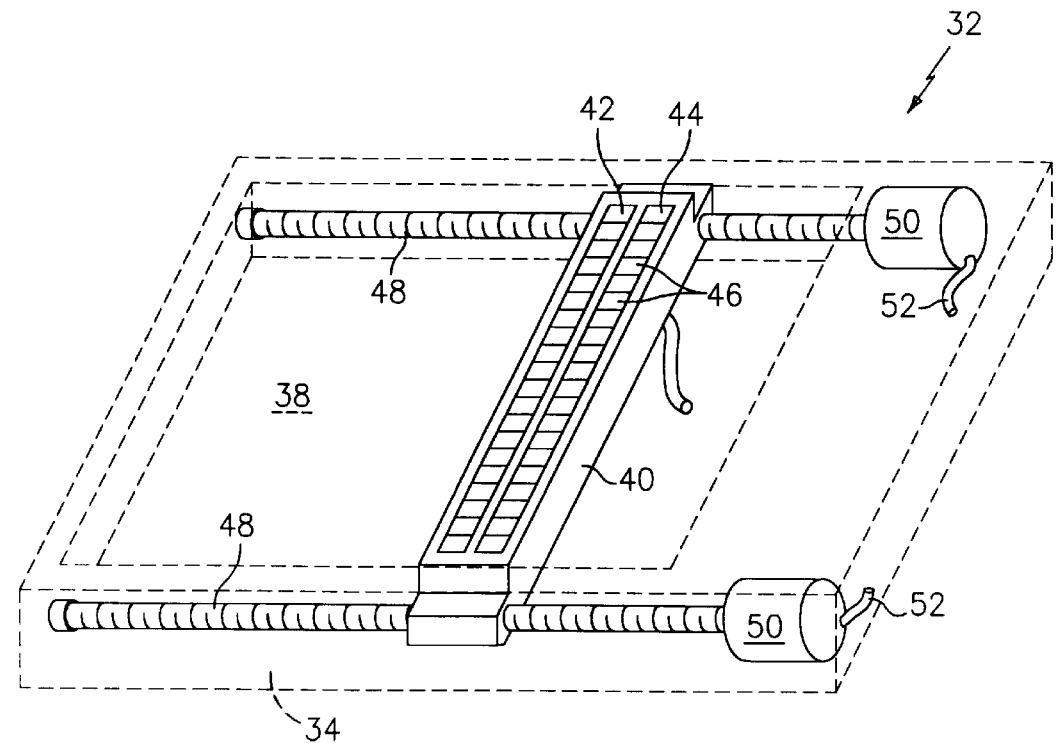
FIGS. 2A and 2B, are respectively, a partial perspective view of the scanning section of FIG. 1 and a partial perspective view of an alternative embodiment of the gantry.
Figure 2B:
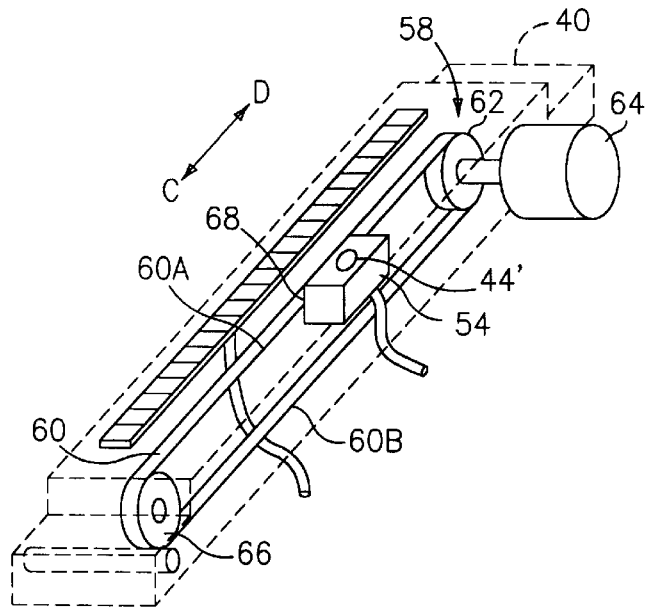

Referring now to FIGS. 2A and 2B, gantry 40 of the present disclosure is described. Gantry 40 includes ultrasonic transducer 44 disposed in fixed relation adjacent to X-ray detector 42, and is positioned beneath window 38 so that X-ray detector 42 and ultrasound detector 44 generate X-ray and ultrasound images, respectively, of tissue disposed on window 38. Gantry 40 is arranged for movement within frame 34 on lead screws 48. Lead screws 48 are driven by motors 50, which are in turn coupled via cables 52 to control station 20. Motors 50 are activated responsive to control commands from control station 20 to move gantry 40 along lead screws 48 either in increments, e.g., 1 to 10 mm, in the case of generating an ultrasound images, or in a continuous motion, in the case of X-ray imaging. It is to be understood that control station 20 controls motors 50 to pause at predetermined locations during transit for a period of time sufficient to obtain an ultrasound image of the tissue at that location.

Ultrasonic transducer 44 may include a single piston or annular array transducer or a phased array imaging device constructed in accordance with previously known design techniques. Such devices permit beam-focussing of ultrasonic energy to provide high resolution images of the internal structures of a patient's tissue. The ultrasound transducers combine both transmit and receive functions that are switched, respectively, between transmitting and receiving operational modes at times selected by the microprocessor of the control station.

In particular, in the embodiment of FIG. 2A, ultrasonic transducer 44 is a linear array of piezoelectric elements 46, and may include a series of layers including copolymers of vinylidene fluoride (VDF) and trifluoroehtylene (TrFE), for example, available from Toray Industries, Kamakura, Japan. Use of such materials to form ultrasonic transducers is described in Ohigashi et al., "Piezoelectric and Ferroelectric Properties of P(VDF-TrFE) Copolymers And Their Application To Ultrasonic Transducers", page 189 et seq., in *MEDICAL APPLICATIONS OF PIEZOELECTRIC POLYMERS* (Galetti et al. editors), Gordon and Breach Science Publishers S.A. (1988). An example of a integrated-silicon VDF-TrFE acoustic transducer array, demonstrated for use diagnostic imaging is described in the above-mentioned Ohigashi et al. reference. Such arrays exhibit a low degree of array element cross-coupling, may be easily fabricated in high density, and provide excellent acoustic impedance matching to biological tissue.

With respect to FIG. 2B, an alternative embodiment is described having ultrasonic transducer 44'. Ultrasonic transducer 44' includes an annular array mounted on carriage 54, which is movable in the transverse directions C and D within gantry 40 on cable arrangement 58. In the illustrative embodiment of FIG. 2B, cable 60 runs on drive wheel 62 of motor 64 at one end and on pulley 66 at the other end, to form upper and lower flights 60A and 60B, respectively. Carriage 54 is fixed to upper flight 60A of cable 60 at point 68 so that carriage 54 moves in directions C and D in response to movement of upper flight 60A. Motor 64, which is supported on gantry 40, enables precise lateral positioning of carriage 54 and thus transducer 44'. Alternatively, a toothed belt and gear arrangement may be substituted for the cables, pulleys, drive wheels and lead screws of the above-described illustrative embodiments.

Because the internal structure and operation of ultrasonic transducers 44 and 44' are per se known, the specific internal configurations of those components forms no part of the present disclosure. Either implementation of ultrasonic transducer 44 or 44' preferably operates in a range of about 2 to 15 MHZ. More preferably, the signal produced by the transducer in the transmit mode is a 10 MHZ burst having a 100 dB bandwidth. To improve the transfer of acoustic energy, the ultrasonic transducer component of gantry 40 is preferably acoustically coupled to a lower surface of window 38 using an appropriate coupling agent such as, for example, glycerol.

In yet further alternative embodiments, X-ray detector 42 and ultrasound transducer 44 may be supported on separate gantries (not shown). In this case, the ultrasound transducer gantry can be moved to a distal or proximalmost position (in direction A or B), so that it does not interfere with the radiogram exposure. Alternatively, the ultrasound gantry may be hinged to swing away from window 38, thus providing clear access for an X-ray exposure. These alternatives are especially useful if the gantry carrying the ultrasound transducer overlaps the area of a two-dimensional X-ray detector.

Still referring to FIGS. 1 and 2, window 38 includes a high performance acoustically transparent ("sonolucent") and X-ray transparent ("radiolucent") sheet that is sufficiently rigid to serve as a tissue support. In particular, it is preferred that window 38 have sufficient rigidity so that the local slope of the plate, under load, does not about exceed one degree from the horizontal within the scan area. For further rigidity, window 38 may include metal reinforcing bars along its edges, outside of the scan area.

Window 38 preferably includes a sheet of Kapton®, a registered trademark of E.I. Du Pont de Nemours and Company, Wilmington, Del., for polyimide compounds, as such material provides both the requisite sonolucent/radiolucent qualities and rigidity to serve as a tissue support. In particular, applicant believes that a twenty-five (25) micron (1 mil) thickness of Kapton®, when used for window 38, is expected to cause less than 3 dB transmission loss in acoustic energy, while providing a tensile strength equivalent to that of a 2 mm thick polycarbonate plate. In addition, Kapton® is unaffected by exposure to X-ray radiation. The required thickness of the material used to create window 38 will of course depend on the dimensions of the window and the particular support structures chosen.

Other materials suitable for use in making a radiolucent and sonolucent window 38 include Surlyn® ionomers, such as Surlyn® 8940, available from E.I. Du Pont de Nemours and Company, Wilmington, Del., and polymethyl pentenes, such as TPX® MX-002, TPX® 95 and MX-004, available from Mitsui & Co., Tokyo, Japan. Plates of these materials also provide sufficient rigidity to meet the above-defined deflection criterion if adequately reinforced around the periphery. Of the two materials, the polymethyl pentenes, and TPX® in particular, are preferred due to their lower acoustic attenuation and impedance and higher strength. A sheet of a Surlyn® ionomer can also be used, although this material is softer and the acoustic losses are expected to be approximately double that of TPX® material.

Figure 3:
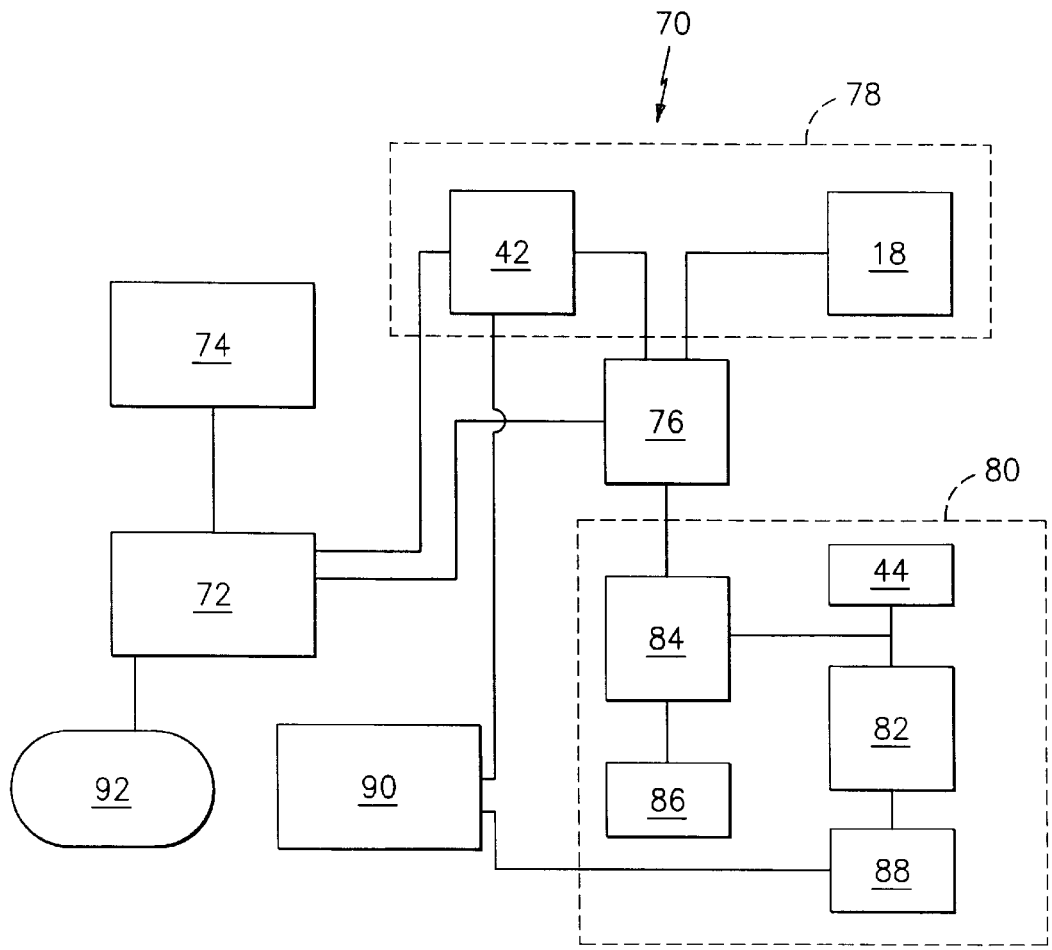
FIG. 3 is a block diagram of the components of an imaging system constructed in accordance with the present disclosure.

Referring now to FIG. 3, illustrative control circuit 70 of control station 20 is described. Circuit 70 includes microprocessor 72 that runs system software 74, gantry motor controller 76, X-ray control circuit 78 and ultrasound control circuit 80. Gantry motor controller 76 is responsive to commands issued by microprocessor 72 to move gantry 40 to perform either X-ray imaging or ultrasound imaging. X-ray control circuit 78 includes circuitry for activating X-ray tube 18, acquiring X-ray image data from X-ray detector 42, and synchronizing movement of X-ray tube 18 along horizontal support 14 with gantry 40. Ultrasound control circuit 80 includes receiving circuit 82, transmit/receive switch 84, drive circuit 86 and analog to digital converter 88. Control station 20 further includes storage device 90 (i.e., a magnetic disk drive) and display 92 electrically coupled to control circuit 70.

Microprocessor 72, which may be an IBM-compatible PC, is programmed to selectively activate either the X-ray imaging system or the ultrasound imaging system, or both, responsive to commands input at keyboard 21 of control station 20. In accordance with the principles of the present disclosure, microprocessor 72 may be programmed to perform both X-ray and ultrasound imaging of tissue disposed above window 38. In particular, as a first step in the operation of imaging apparatus 10, microprocessor 72 may first issue commands to X-ray controller circuit 78 that cause activation of X-ray tube 18 and X-ray detector 42. Gantry 40 is moved in synchrony with X-ray tube 18 (assuming a line source) to generate data corresponding to a two-dimensional X-ray image. An example of a drive assembly for synchronizing the movement of a line source and detector is disclosed in above-incorporated U.S. Pat. Nos. 4,696,022 and 4,692,937. Data resulting from activation of the X-ray imaging subsystem is stored with positional information, described below, in storage device 90 for later analysis and display.

During a next step of operation of imaging apparatus 10, microprocessor 72 issues commands to ultrasound control circuit 80 to generate data corresponding to a series of two-dimensional ultrasound images at selected spaced-apart locations during transit of gantry 40. Specifically, transducer 44 is energized by drive circuit 86 to emit ultrasonic signals. Once the transducer has emitted acoustic energy for a suitable period, the transducer is switched to receiving mode by switch 84. As transducer 44 responds to the echoes of the emitted signals, it generates electrical signals in receiving circuit 82.

Receiving circuit 82 preferably has a wide dynamic range, for example, 100 dB, to enable high contrast resolution. Since the receiving circuit records the transmitted pulse as well as the returning echoes, the first $T_0$ microseconds corresponding to the time-of-flight from the transducer surface to the tissue is ignored. Receiving circuit 82 also includes an automatic gain amplifier that can be adjusted to compensate for the attenuation of the returning signal. The received signal is therefore amplified and processed by receiving circuit 82 before being fed to analog-to-digital converter circuit 88. Analog-to-digital converter translates the analog electrical echo signals into digital signals, which are in turn stored in storage device 90.

Microprocessor 72 monitors gantry motor controller 76 and continuously computes the position of X-ray detector 42 and ultrasound transducer 44. The digitized data corresponding to the gantry location at each data acquisition location, for both X-ray data and ultrasound data, is stored in storage device 90 together with the corresponding image data at that location. System software 74 enables the image data stored in storage device 90 to be manipulated so that, for example, correlated X-ray and ultrasound images may be displayed on display 22, or holographic views generated and viewed from different angles.

Figure 4:
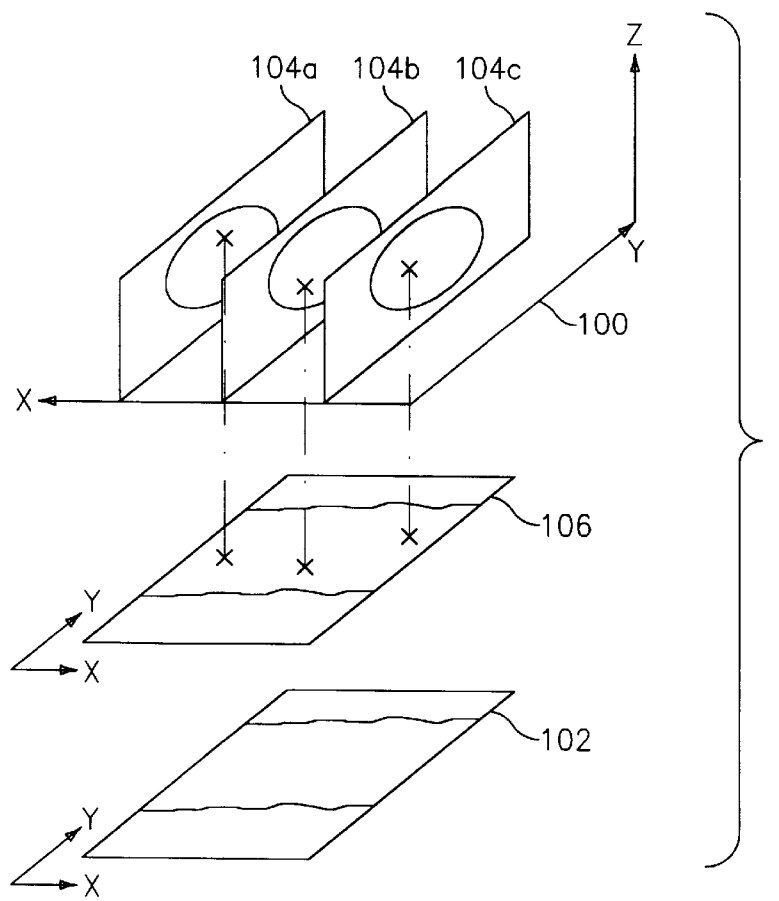
FIG. 4 is a perspective view of ultrasound and X-ray images generated in accordance with the methods of the present disclosure.
Figure 5:
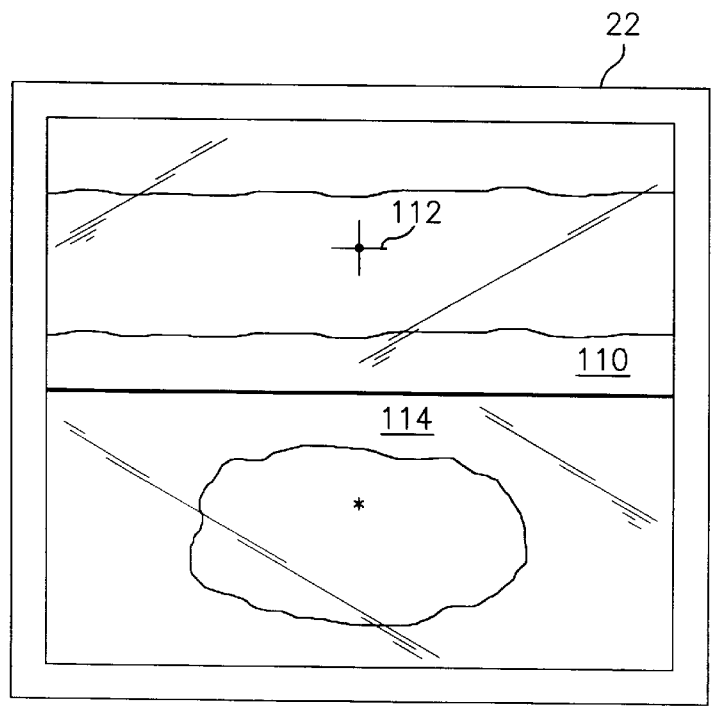
FIG. 5 is an illustrative view of a display showing X-ray image and ultrasound image display windows.

Referring now to FIGS. 1, 4 and 5, a method of viewing the stored X-ray and ultrasound image data acquired with apparatus 10 of the present disclosure is described. As shown in the uppermost portion of FIG. 4, an imaginary three dimensional coordinate system 100, consisting of X, Y, Z directions, can be imposed on apparatus 10 of FIG. 1 so that the X-Y plane coincides with the surface of window 38, and the Z axis corresponds to elevation above examination table 12. Activation of the X-ray imaging subsystem of apparatus 10 generates data forming X-ray image 102 in the X-Y plane. Subsequent activation of ultrasound transducer 44 generates image frames 104a–104c, in the X-Z plane, of the interior of tissue disposed on window 38. It is to be understood that each of image frames 104a–104c corresponds to a different displacement of ultrasound transducer 44 along window 38 in directions A-B.

As shown in FIG. 5, system software 74 preferably provides programming that enables display of X-ray image 102 in X-ray image display window 110 of display 22. Based upon the selection of a feature in the X-ray image display window 110, for example, using cursor 112 in the X-ray image display window, system software 74 provides the corresponding ultrasound image data in separate ultrasound image display window 114. By examining the ultrasound image corresponding to the feature observed in the X-ray image, the clinician can determine the volumetric location of the feature.

In addition, since cross-sectional views in the X-Z plane are stored at predetermined intervals for the tissue, it is possible to sum each propagation line and obtain a two-dimensional projection map of the tissue ultrasound attenuation for comparison to the X-ray image. In particular, the ultrasound data stored in each frame 104a–104c of FIG. 14 may be summed in the Z direction to provide a single line in the X-Y plane, thus generating a two dimensional ultrasound image 106. By projecting the ultrasound data in the X-Z plane into a single line in the X-Y plane to create image 106, tissue abnormalities (indicated by x's in FIG. 4) can be displayed in the same format as X-ray image 102. When ultrasound image 106 as obtained above is then overlaid on X-ray image 102, tissue abnormalities may be readily isolated and identified. Ultrasound image 106 and X-ray image 102 may be color-coded to speed this identification process.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An apparatus for imaging biological tissue, comprising:
   a table having a radiolucent and sonolucent window on which biological tissue may be positioned;
   an X-ray source movably disposed above the table that emits X-ray radiation;
   an X-ray detector movably disposed beneath the window to receive X-ray radiation emitted by the X-ray source that passes through the biological tissue, wherein the X-ray detector is synchronously movable with the X-ray source relative to the window to facilitate generating X-ray data to form an X-ray image;
   an ultrasonic transducer positioned adjacent the X-ray detector and acoustically coupled to the window, the ultrasonic transducer generating an ultrasound image of the biological tissue; and
   a drive assembly for moving the ultrasonic transducer through a predetermined path beneath the window while the biological tissue remains immobilized on the table, so that the ultrasonic transducer generates a plurality of ultrasound images of the biological tissue that are in registration with the X-ray image.

2. The apparatus as defined in claim 1, wherein the X-ray source emits X-ray radiation along a line.

3. The apparatus as defined in claim 2, wherein the X-ray detector is a digital line detector.

4. An apparatus for imaging biological tissue, comprising:
   a table having a radiolucent and sonolucent window on which biological tissue may be positioned;
   an X-ray source disposed above the table that emits X-ray radiation;
   an X-ray detector disposed beneath the window to receive X-ray radiation emitted by the X-ray source that passes through the biological tissue, the X-ray detector generating X-ray data to form an X-ray image;
   an ultrasonic transducer positioned adjacent the X-ray detector on a movable support and acoustically coupled to the window, wherein the moveable support undergoes relative motion with respect to the biological tissue to facilitate the ultrasonic transducer generating an ultrasound image of the biological tissue; and
   drive assembly for moving the ultrasonic transducer through a predetermined path beneath the window while the biological tissue remains immobilized on the table, so that the ultrasonic transducer generates a plurality of ultrasound images of the biological tissue that are in registration with the X-ray image.

5. The apparatus as defined in claim 1, further comprising a gantry, the gantry housing the ultrasonic transducer and being coupled to the drive assembly.

6. The apparatus as defined in claim 5, wherein the ultrasonic transducer comprises an annular array carried on a laterally moveable carriage.

7. The apparatus as defined in claim 6, wherein the drive assembly further comprises:
   a motor;
   a lead screw coupled to the gantry and to the motor; and
   circuitry for controlling operation of the motor.

8. The apparatus as defined in claim 1, wherein the ultrasonic transducer comprises a multiplicity of piezoelectric transducer elements.

9. The apparatus as defined in claim 8, further comprising control circuitry for activating the multiplicity of piezoelectric transducer elements to form an ultrasound image of the biological tissue.

10. The apparatus as defined in claim 1 wherein the table comprises a plurality of removable patient support sections, and wherein the X-ray detector, ultrasonic transducer and drive assembly are housed in a scanning section, the scanning section movable to a desired location on the table.

11. Apparatus for imaging biological tissue, comprising:
    a table having a plurality of patient support sections and a scanning section; and
    an X-ray source disposed above the table that emits X-ray radiation;
    wherein the scanning section includes:
       a radiolucent and sonolucent window on which biological tissue may be positioned, the scanning section housing including:

an X-ray detector movably disposed beneath the window to receive X-ray radiation emitted by the X-ray source that passes through the biological tissue, wherein the X-ray detector is synchronously with the X-ray source relative to the window to facilitate generating X-ray data to form an X-ray image;

an ultrasonic transducer positioned adjacent the X-ray detector and acoustically coupled to the window, the ultrasonic transducer generating an ultrasound image of the biological tissue; and a drive assembly for moving the ultrasonic transducer through a predetermined path beneath the window while the biological tissue remains immobilized on the table, so that the ultrasonic transducer generates a plurality of ultrasound images of he biological tissue that are in registration with the X-ray image.

12. The apparatus as defined in claim 11, wherein the X-ray source emits X-ray radiation along a line.

13. The apparatus as defined in claim 12, wherein the X-ray detector is a digital line detector.

14. Apparatus for imaging biological tissue, comprising:

a table having a plurality of patient support sections and a scanning section; and an X-ray source disposed above the table that emits X-ray radiation;

wherein the scanning section includes:

a radiolucent and sonolucent window on which biological tissue may be positioned, the scanning section housing including:

an X-ray detector disposed beneath the window to receive X-ray radiation emitted by the X-ray source that passes through the biological tissue, the X-ray detector generating X-ray data to form an X-ray image;

an ultrasonic transducer positioned adjacent the X-ray detector on a moveable support on a moveable support and acoustically coupled to the window, the ultrasonic transducer generating an ultrasound image of the biological tissue upon relative motion of the moveable support with respect to the biological tissue upon relative motion of the moveable support with respect to the biological tissue; and a drive assembly for moving the ultrasonic transducer through a predetermined path beneath the window while the biological tissue remains immobilized on the table, so that the ultrasonic transducer generates a plurality of ultrasound images of he biological tissue that are in registration with the X-ray image.

15. The apparatus as defined in claim 11, further comprising a gantry, the gantry housing the ultrasonic transducer and being coupled to the drive assembly.

16. The apparatus as defined in claim 15, wherein the ultrasonic transducer comprises an annular array carried on a laterally moveable carriage.

17. The apparatus as defined in claim 16, wherein the drive assembly further comprises:

a motor;

a lead screw coupled to the gantry and to the motor; and circuitry for controlling operation of the motor.

18. The apparatus as defined in claim 11, wherein the ultrasonic transducer comprises a multiplicity of piezoelectric transducer elements.

19. The apparatus as defined in claim 18, further comprising control circuitry for activating the multiplicity of piezoelectric transducer elements to form an ultrasound image of the biological tissue.

20. The apparatus as defined in claim 1 wherein the plurality of patient support sections are removable and the scanning section is selectively movable to a desired location on the table.

21. A method for imaging biological tissue, comprising the steps of:

providing a table having a radiolucent and sonolucent window on which biological tissue may be positioned;

generating X-ray data to form an X-ray image by moving an X-ray detector synchronously with an X-ray source; and moving an ultrasonic transducer through a predetermined path beneath the window while the biological tissue remains immobilized on the table, so that the ultrasonic transducer generates a plurality of ultrasound images of the biological tissue that are in registration with the X-ray image.

* * * * *